United States Patent [19]

Laible et al.

[11] Patent Number: 4,809,850
[45] Date of Patent: Mar. 7, 1989

[54] SELF-CLOSING SHARPS CONTAINER WITH HAND PROTECTION

[75] Inventors: Rodney Laible, Bennington; Daniel Brown, Omaha, both of Nebr.

[73] Assignee: Custom Medical Plastics, Inc., Omaha, Nebr.

[21] Appl. No.: 174,192

[22] Filed: Mar. 28, 1988

[51] Int. Cl.⁴ .............................................. B65F 1/16
[52] U.S. Cl. .................................... 206/366; 220/1 T
[58] Field of Search ................. 220/1 T; 206/366, 365

[56] References Cited

U.S. PATENT DOCUMENTS

| | | | |
|---|---|---|---|
| 1,202,469 | 10/1916 | Anzevino. | |
| 4,121,755 | 10/1978 | Meseke et al. | 206/366 |
| 4,315,592 | 2/1982 | Smith | 206/366 |
| 4,380,292 | 4/1983 | Cramer | 206/366 |
| 4,494,652 | 1/1985 | Nelson et al. | 206/63.5 |
| 4,576,281 | 3/1986 | Kirksey | 206/366 |
| 4,662,516 | 5/1987 | Baker, Sr. et al. | 206/366 |
| 4,674,676 | 6/1987 | Sandel et al. | 206/366 |
| 4,714,168 | 12/1987 | Johnson et al. | 206/366 X |
| 4,715,498 | 12/1987 | Hanifl | 206/366 |

OTHER PUBLICATIONS

Puncture Proof/Point-of-Use Protection Against Sharps-Winfield.
In-Room Sharps Disposal System-Sage Products, Inc.
Is Sharps Disposal Safe in Your Hospital?-American Hospital Supply.
Wall-Safe-American Hospital Supply.
D.D.Box Sharps Disposal Container.

*Primary Examiner*—William Price
*Attorney, Agent, or Firm*—John A. Beehner

[57] ABSTRACT

A sharps container includes a disposable open topped receptacle having a lid with an elongated opening therethrough and a closure flap pivotally supported adjacent the opening for pivotal movement between positions for opening and closing the opening. The closure flap is self-closing, being biased to the closed position. The disposable receptacle may be supported within a reusable cabinet having upright spaced-apart end walls which extend upwardly above the lid of the receptacle. A handle on the exterior side of at least one wall is coupled to the closure flap for opening and closing the flap in response to turning movement of the handle. The raised container end walls shield the hand of an operator on the handle from sharps being inserted into the container opening.

25 Claims, 7 Drawing Sheets

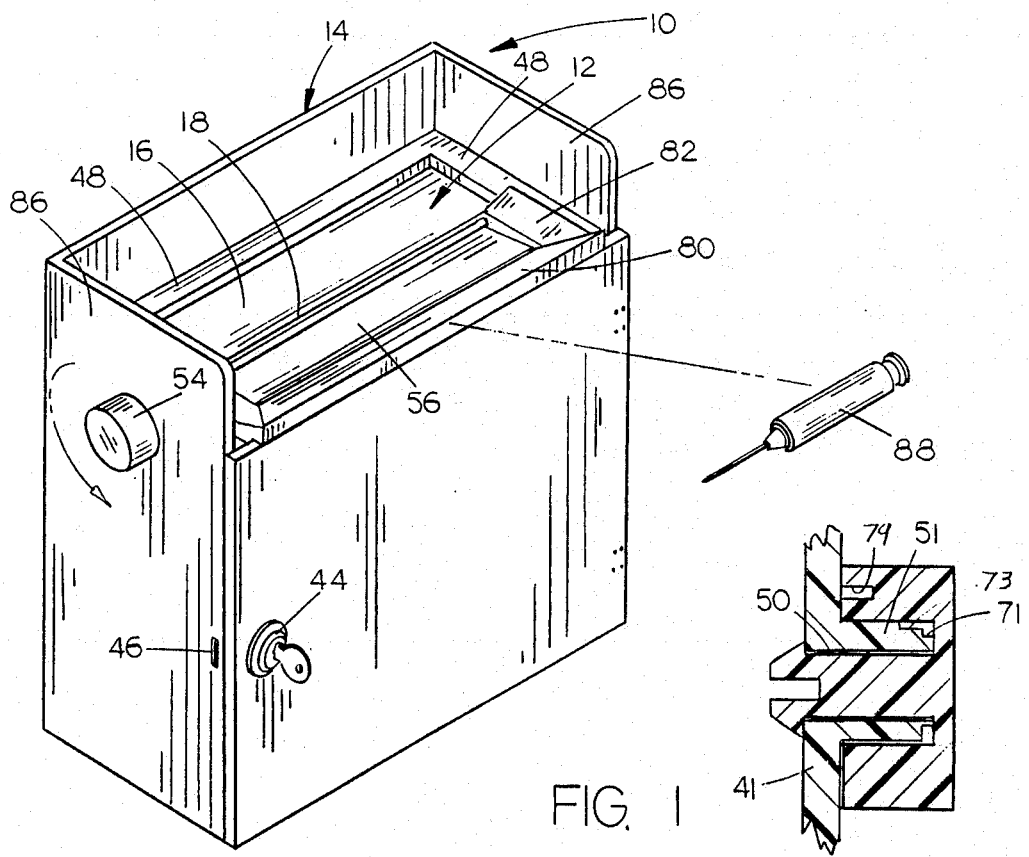
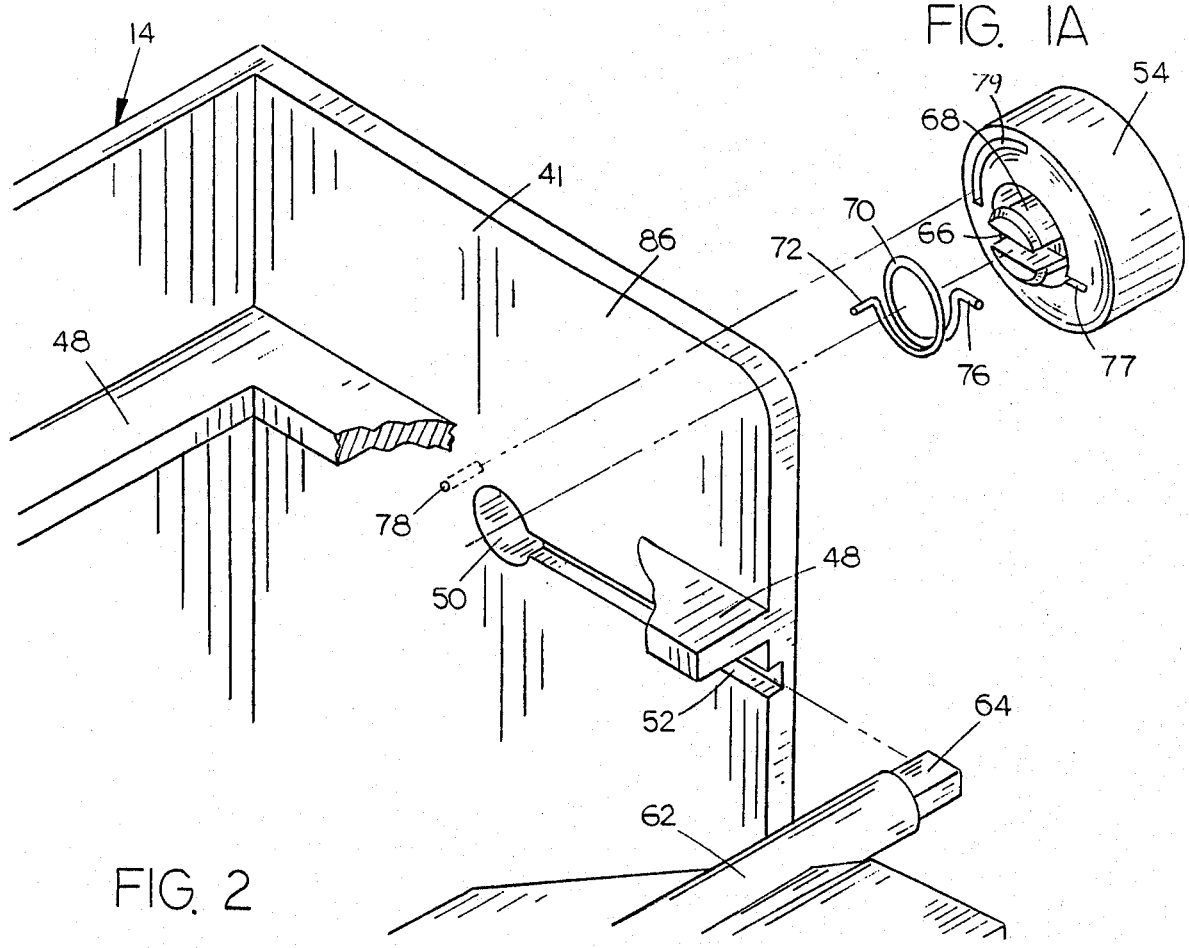

SELF-CLOSING SHARPS CONTAINER WITH HAND PROTECTION

BACKGROUND OF THE INVENTION

The present invention is directed generally to a sharps container for collecting and storing used syringes, hypodermic needles and other infectious waste.

Particularly in view of the growing concern about exposure to AIDS, there is a need for improved sharps containers which afford better protection for the doctors, nurses and technicians who use and handle the containers. Sharps containers have commonly been provided with a relatively large circular opening through which sharps are dropped in a vertical orientation for haphazard collection within the container. As the container fills, one runs the risk of a previously inserted needle protruding from the opening where it can stab the hand of the next operator to insert something into the container. Likewise, the side walls of relatively soft or thin-walled material could be pierced by any one of the haphazardly arranged needles within the container thereby possibly exposing to infectious disease the next person to brush by the container. These problems have been partially addressed by such recent sharps containers as that disclosed in Hanifl, U.S. Pat. No. 4,715,498 which shows a mailbox-like structure having a tilt pan which tips outwardly for receiving a needle or the like and which tips inwardly for depositing the needle in the container. The handles for operating the tilt pan, however, are situated on the container top wall immediately adjacent the opening such that the hand operating the levers is necessarily positioned dangerously close to the opening so as to be exposed to stabbing by a carelessly disposed of needle. Furthermore, that device is not self closing so that if an operator does not manually pivot the tilt pan to the closed position, an infectious needle or the like may remain seated in the tilt pan where it could be accidently engaged by the hand of an operator.

Accordingly, a primary object of the invention is to provide an improved sharps container.

Another object is to provide a sharps container wherein the hand operating the closure member is protected from being accidently stabbed by sharps being inserted into the container.

Another object is to provide an improved sharps container having an automatic self-closing flap over the filler opening.

Another object is to provide a sharps container wherein the handle is situated on the container end wall in substantial spaced relation from the top opening to prevent accidental contamination of the handle by sharps being inserted into the opening.

Another object is to provide a sharps container having an elongated filler opening for convenient and substantially unobstructed placement of horizontally disposed sharps into the opening.

Another object is to provide an improved sharps container having a closure flap situated such that the sharps within a filled container obstruct opening movement of the closure flap.

Another object is to provide an improved sharps container wherein the filler opening is surrounded by inclined surfaces for guiding sharps toward and into the opening.

Another object is to provide a sharps container wherein the closure flap assists with horizontally orienting the sharps for placement into the container.

Another object is to provide an improved sharps container which is simple and rugged in construction, inexpensive to manufacture and efficient in operation.

SUMMARY OF THE INVENTION

The sharps container of the present invention includes a disposable container having an elongated opening through the top surface thereof and a closure flap pivotally supported adjacent the opening for pivotal movement between an open position permitting the insertion of sharps into the container through the opening and a closed position substantially closing the opening. The disposable container may be supported within a reusable cabinet having upright spaced-apart end walls with the container supported within the cabinet at a position such that the end walls extend upwardly above the top of the container. A handle on the exterior side of at least one end wall is coupled to the closure flap for pivotally moving the flap between the closed and open positions while the top portion of the end wall on which the handle is mounted shields the hand, which is turning the handle, from sharps being inserted into the container opening. The disposable container may be provided as an open-topped receptacle designed to be closed by a lid having the elongated opening formed therein so that the separate receptacles and lids may be nested and stacked for compact transport and storage. An important feature of the invention is the automatic self-closing action of the closure flap. This may be accomplished either by gravity or with a power assist such as from a spring.

The closure flap may be provided with stub shafts extended from the opposite ends thereof, which stub shafts have flattened ends which, when horizontally disposed, are slidable into and through guide slots in the cabinet end walls for properly aligning the closure flap with a matching slot of the spring biased handle mounted on the cabinet end wall. Thus no mechanical aptitude is required for assembling and properly fitting the disposable container into the cabinet.

Border strips on opposite ends of the elongated opening protrude above the top surface of the lid and present top surfaces inclined downwardly and toward the opening for guiding any misdirected sharps into and through the opening. The pivotal closure flap has an interior wing which engages sharps within a filled container to prevent opening of the flap. The filled container can then be easily sealed shut by simply pressing the closure flap toward the opening where it snap fits below a set of lock tabs. The resulting sharps container is thus simple to assemble and use while affording protection to even a careless operator against accidental stabbing by a possibly infectious needle.

BRIEF DESCRIPTION OF THE DRAWINGS

FIG. 1 is a perspective view of the sharps disposal apparatus of the invention;

FIG. 1A is a front sectional view through the handle on the cabinet end wall;

FIG. 2 is an enlarged partial exploded view illustrating the spring biased handle for rotating the pivot closure of the invention;

DESCRIPTION OF THE PREFERRED EMBODIMENT

Figure 3:
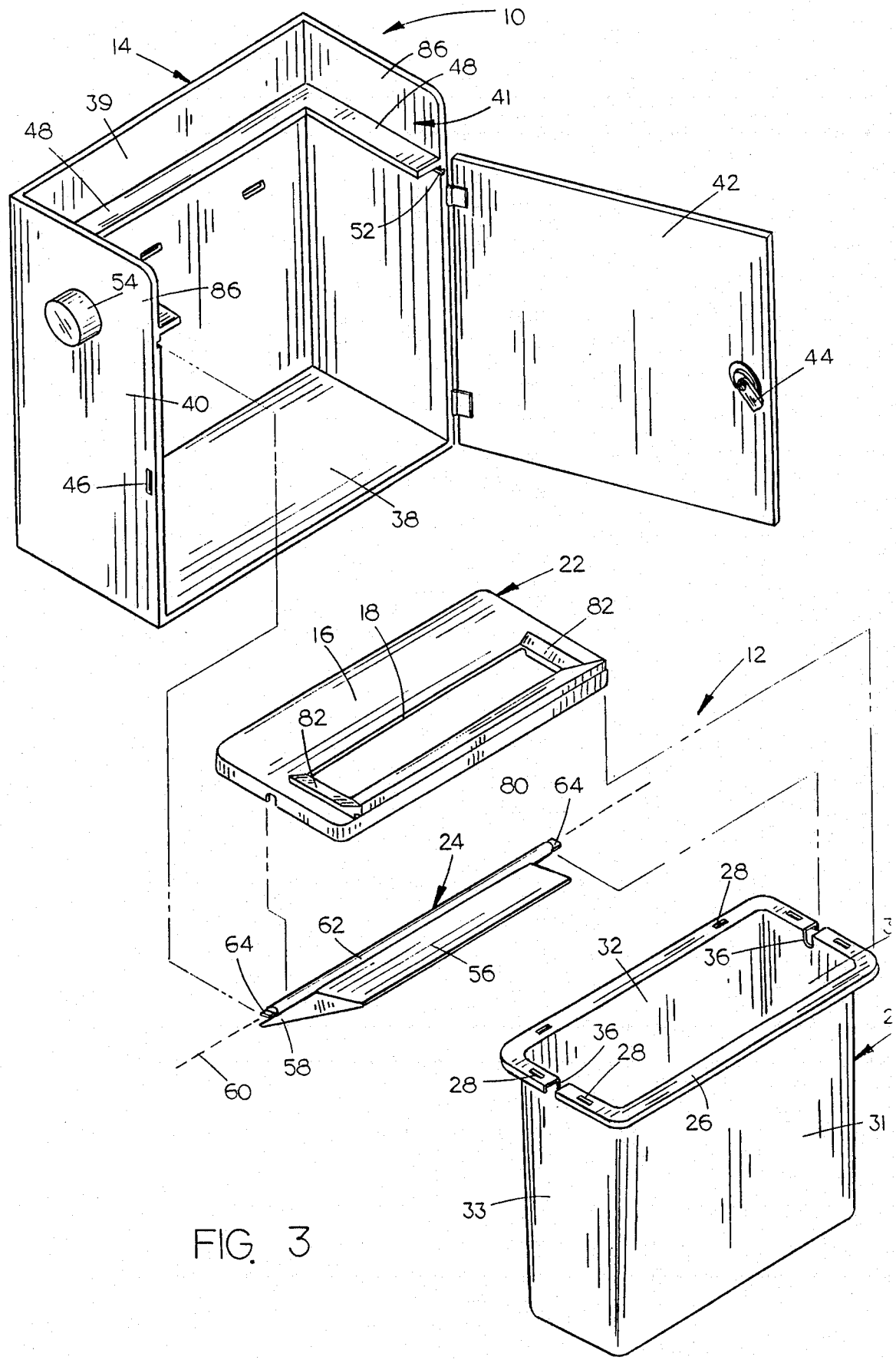
FIG. 3 is an exploded perspective view of the invention.
Figure 4:
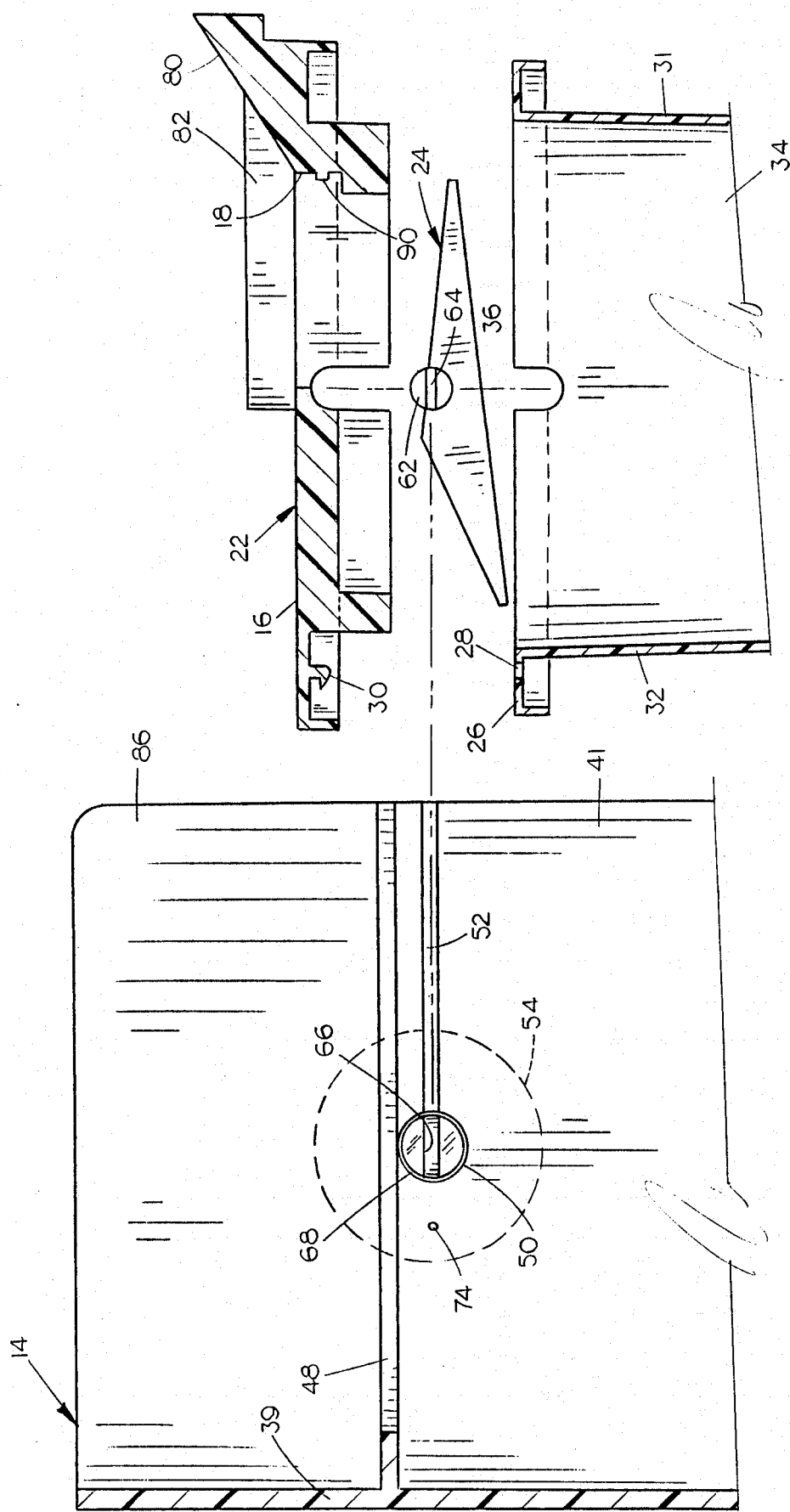
FIG. 4 is an enlarged partial exploded side sectional view showing the relation of the pivot closure to the adjacent lid and receptacle.
Figure 5:
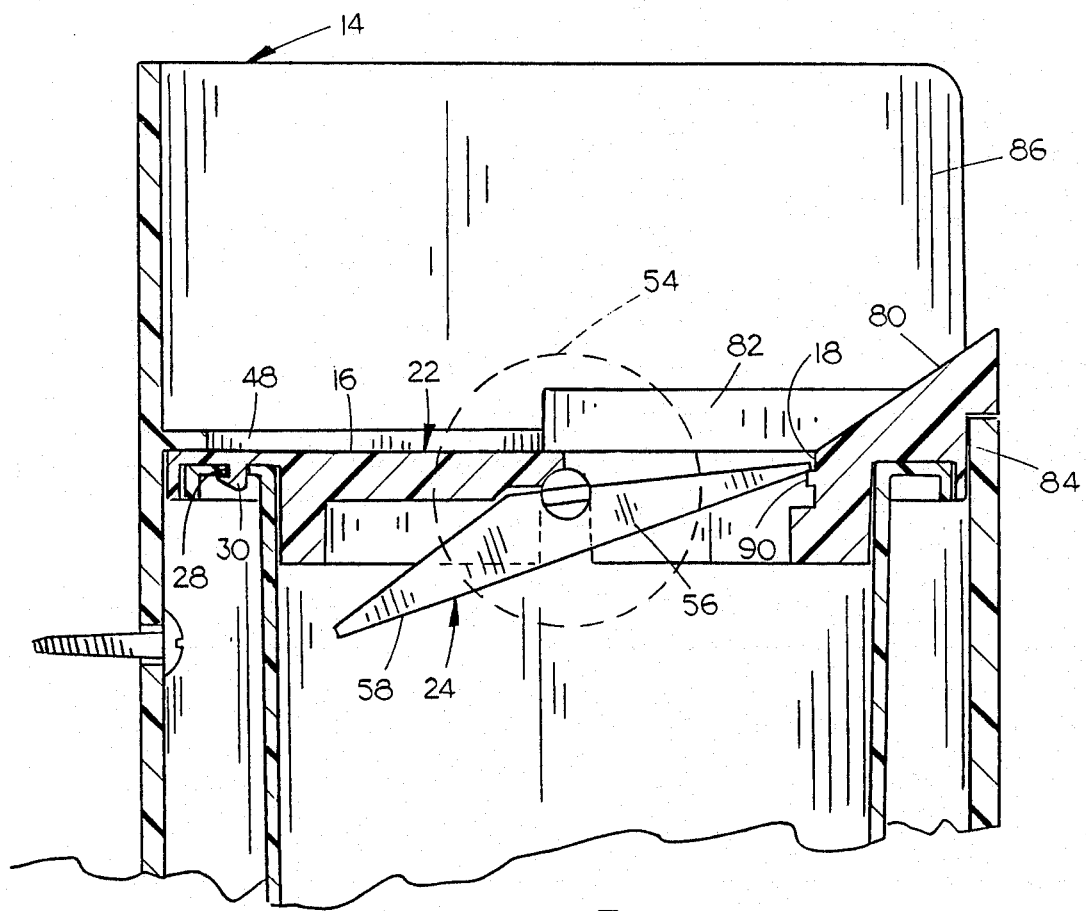
FIG. 5 is a partial side sectional view showing the installed pivot closure in a closed position.

The sharps container 10 of the present invention is illustrated in FIGS. 1-3 and includes a disposable container 12 which is adapted to be housed and supported within a permanent cabinet 14. The disposable container 12 has a top surface 16 having a transversely extended elongated opening 18 formed therein.

As shown in FIG. 3, the disposable container 12 is preferably formed of three separate parts including an open topped receptacle 20, a snap fit lid 22 and a pivotal closure flap 24. Receptacle 20 has a top rim 26 including a series of slots 28 which are adapted to receive corresponding depending lock fingers 30 of lid 22 for a permanent snap fit connection between the lid and receptacle. Alternatively, the lid could be provided with slots and the receptacle rim with upstanding lock fingers or any other suitable connection may be provided. The receptacle is preferably formed with a somewhat downward taper to facilitate nesting a stack of receptacles together for compact shipment and storage. The receptacle includes a front wall 31, rear wall 32 and opposite end walls 33 and 34. The upper edges of end walls 33 and 34 have generally centrally located slots 36 formed therein for pivotally supporting the closure flap 24, as described in further detail below.

Likewise, cabinet 14 includes a bottom wall 38, rear wall 39, opposite upstanding end walls 40 and 41 and a hinged front wall 42 which is pivotally supported on the front edge of end wall 41 and is provided with a lock mechanism 44 for engagement with a slot 46 adjacent the front edge of end wall 40 for securely locking a receptacle into the cabinet. The cabinet furthermore has an interiorly directed shoulder 48 on the interior surface of rear wall 39 and end walls 40 and 41, with the distance between bottom wall 38 and the underside of shoulder 48 being substantially equal to the height of the top surface 16 of the disposable container 12. Thus the disposable container can be slide fit into the cabinet and below shoulder 48.

Referring to FIGS. 1A and 2, each cabinet end wall 40 and 41 is additionally provided with a handle opening 50 an integral external annular bushing 51 and a horizontally disposed guide slot 52 on the interior surface of the end wall extending from the front edge to the handle opening 50 below shoulder 48 for properly orienting the closure flap 24 for engagement with an external handle 54.

The closure flap 24, as shown in FIG. 3, includes a front wing 56 and a rear wing 58 on opposite sides of a pivot axis 60 through a closure shaft 62 having opposite ends extended beyond the wings for pivotal support within the receptacle slots 36. The length of the wings 56 and 58 corresponds to the transverse extent of the receptacle top opening 18 for closing that opening at times. Whereas the closure shaft 62 is illustrated as extending continuously along the length of the wings, it could simply be provided as a pair of stub shafts at opposite ends of the wings or even as holes in opposite ends of the flap for receiving protruding portions of modified handles.

In FIGS. 2 and 3, each end of closure shaft 62 is flattened as at 64 for receipt within a diametrically extended slot 66 through the pivot axis of the stem portion 68 of handle 54. Stem portion 68 is inserted through bushing 51 and handle opening 50 in the cabinet end wall for receiving the flattened end 64 of the closure shaft 62 into the handle slot 66.

To assure alignment between the handle slot 66 and flattened closure shaft ends 64, the guide slots 52 in cabinet end walls 40 and 41 constrain the flattened shaft ends 64 to a horizontal orientation for sliding movement within the guide slots 52.

Likewise, handle 54 is biased to a position corresponding to a horizontal orientation of the handle slot 66. This is accomplished by a coil spring 70 placed in a recess 71 on the end of bushing 51. The spring has an axially bent end 72 adapted for receipt within a small hole 73 in the upstanding wall of recess 71 (FIG. 1A) and an opposite radially bent end 76 for receipt within an interior slot 77 (FIG. 2) of handle 54. Accordingly, upon release of the handle, spring 70 returns it to a position wherein the stem slot 66 is aligned with the cabinet guide slots 52.

In FIG. 1A, it is seen that the handle fits onto bushing 51 with the handle stem in bearing relation with the interior surface of bearing 51 and the outer portion of the handle in bearing relation with the exterior surface of bearing 51. Pivotal movement of the handle is confined to movement between positions corresponding to the open and locked positions of FIGS. 6 and 8 respectively by an integral boss 78 on the exterior surface of cabinet end wall 41, which boss 78 is received within a cam slot 79 on the interior face of handle 54 as shown in FIG. 2. The circumferential extent of slot 79 is preferably about 90°.

FIGS. 4 through 8 illustrate the relative positions of the cabinet 14, receptacle 20, lid 22, closure flap 24 and handle 54 in the assembled container 10. It is seen that the closure flap is pivotally movable between the fully closed or locked position of FIG. 8 and the partially open position illustrated in FIG. 6 in response to turning of either handle 54. Note that the horizontal orientation for the handle stem slot 66 corresponds to the closed position of the closure flap (FIG. 5) with the result that the closure flap is spring biased to that position. It can also be seen in the end views of FIGS. 5 and 6 that the mass of the closure flap longer front wing 56 exceeds the mass of the shorter rear wing 58 with the result that the closure flap is also biased to its closed position of FIG. 5 by gravity. The spring and gravity closure features may be used in the alternative or preferably in combination, as illustrated.

Figure 6:
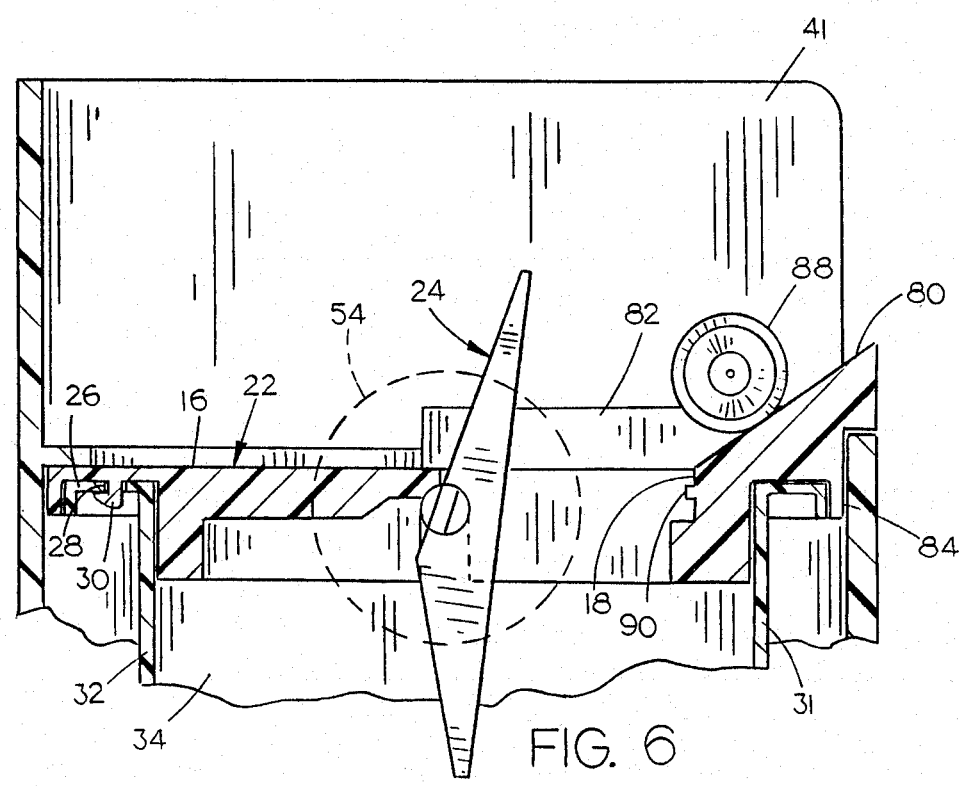
FIG. 6 is a partial side sectional view showing the installed pivot closure in an open position.

Several structural features are incorporated into the sharps container 10 of the invention to assure the safe and convenient disposal of sharps. For example, FIGS. 1, 3 and 6 show that the front and both end edges of the elongated opening 18 in the top of disposable container 12 are bordered by edges presenting top surfaces 80 and 82 which are inclined downwardly and toward the opening for guiding any misdirected sharps into and through the opening 18. It is preferable that the end edges 82 protrude above the top surface 16 of lid 22 to present a barrier between opening 18 and the closure flap handles for shielding the operator's hand on handle 54 from any misdirected sharps.

Furthermore, it can be seen in FIG. 6 that the front edge 80 extends forwardly beyond the front edges of end walls 40 and 41 and is undercut at the lower front edge to present a recess 84 for receiving the upper edge of the container front wall 42. Thus, the top edge of the container front wall 42 is shielded from exposure to contact by any possible infectious sharps.

A very important feature of the invention is the function of the top portion of the cabinet end walls 40 and 41 for shielding the operator's hand on handle 54 from sharps being inserted into the container 12 within cabinet 14. Each end wall includes an upper portion 86 which protrudes above the shoulder 48 and thus above the container lid 22 and which extends from the front edge to the back edge of the end wall. These upper portions 86 cooperate with the placement of the handles on the exterior side of end walls 40 and 41 to maximize the structural barrier between each handle 54 and opening 18. Thus the handles 54 are spaced outwardly away from the opening beyond the ends of the container lid and are shielded from the opening 18 both by the raised edges 82 at the ends of the opening and the upper portions 86 of the cabinet end walls.

Figure 11:
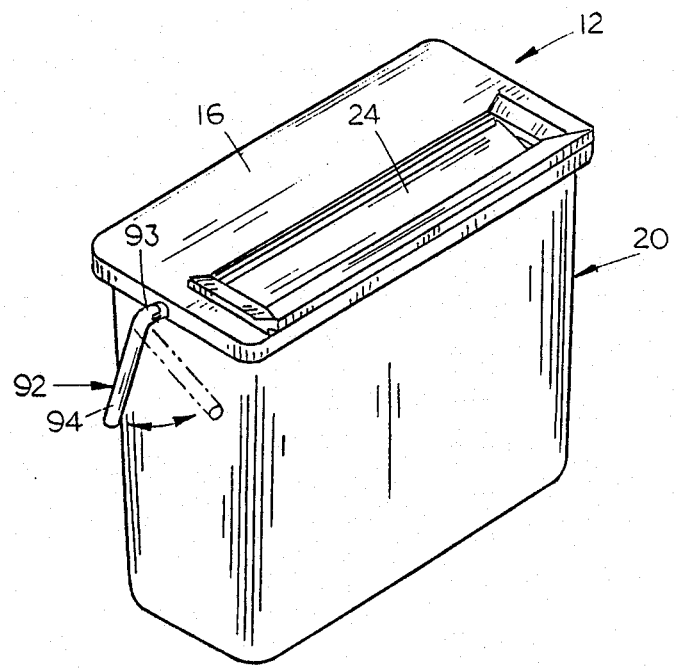
FIG. 11 is a perspective view of the disposable container with handles attached to the ends of the closure flap shaft.

Even if the disposable container 12 is used alone apart from cabinet 10, with handles 92 placed directly onto the ends of the closure shaft, as shown in FIG. 11, the top corner of the lid which separates the top surface 16 from the container end walls 33 contributes to the shielding of the operator's hand from sharps being inserted into the opening 18.

Handle 92 includes a slotted connector 93 adjacent one end for connection to the flattened end 64 of the closure flap shaft 62, and an elongated grip 94 extending downwardly and rearwardly from the connector 93 in the closed position of the closure flap and downwardly and forwardly from the connector, as shown in dotted lines in FIG. 11, in the open position of the closure flap, whereby the operator's hand on handle 92 remains well shielded and spaced from opening 18 at all positions of the handle.

Figure 7:
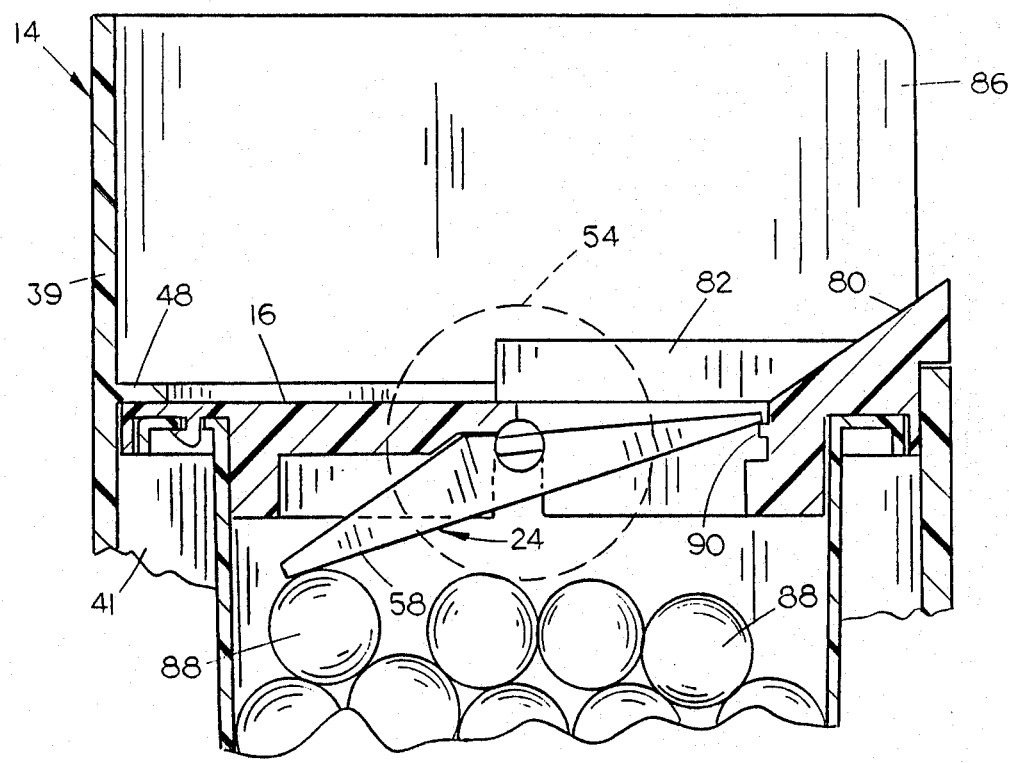
FIG. 7 is a partial side sectional view of the apparatus showing the pivot closure blocked from opening by engagement with sharps within a filled container.

Another feature of the invention is the function of the rear wing 58 of closure flap 24 for preventing opening movement of the closure flap when the container is filled. Referring to FIG. 7, it is seen that the rear wing 58 extends generally rearwardly below the top surface of the lid in the closed position of the closure flap 24 but is pivoted downwardly into the container upon pivotal movement of the closure flap to the open position as illustrated in FIG. 6. That opening movement is blocked by engagement of the rear wing 58 with sharps 88 within a substantially filled container as indicated in FIG. 7.

Figure 8:
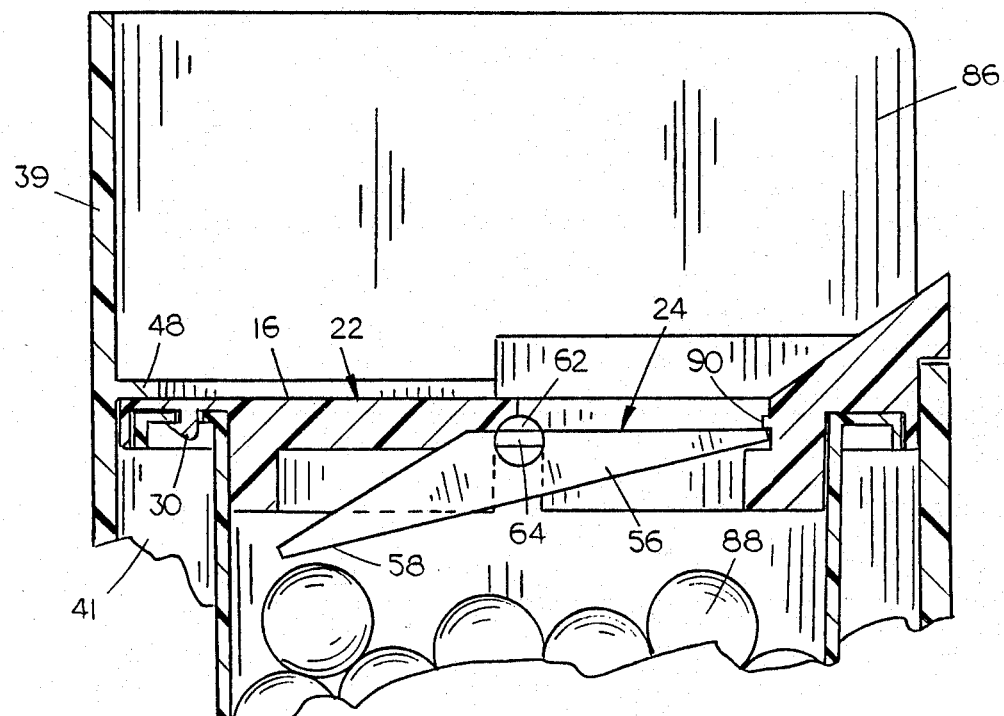
FIG. 8 is a partial side sectional view showing the pivot closure snap locked in a closed position.
Figure 9:
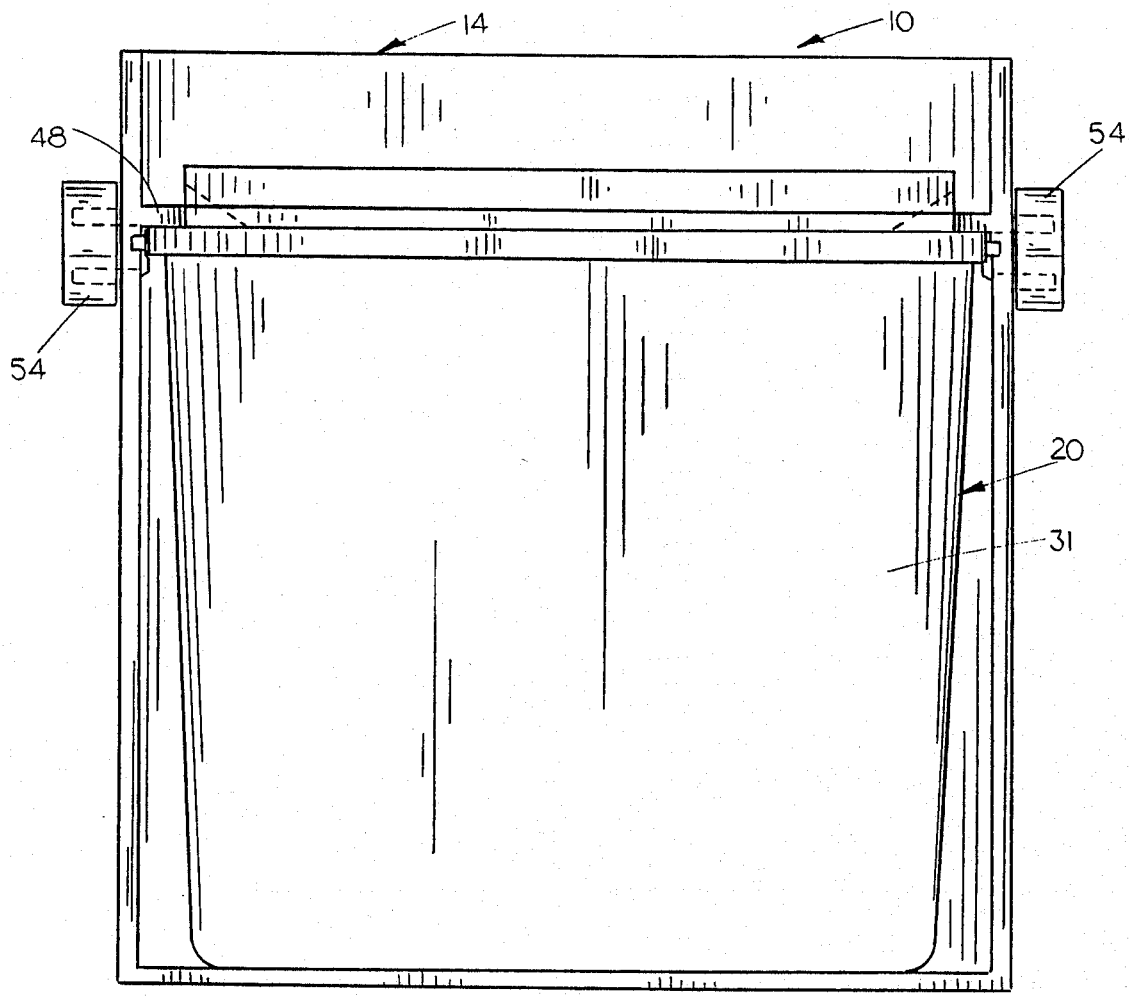
FIG. 9 is a front view of the open cabinet with the disposable container installed therein.
Figure 10:
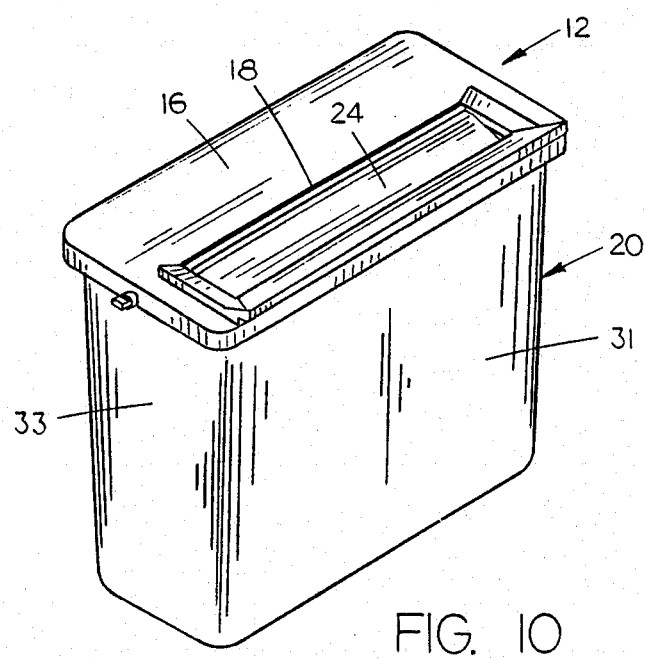
FIG. 10 is a perspective view of the disposable container of the invention.

At that point, the closure flap can be permanently locked in a closed position by pressing down on the front wing 56, as illustrated in FIG. 8, to force the front edge of front wing 56 downwardly past a couple of lock taps 90, which thereafter block opening movement of the closure flap. The construction of the disposable container 12 is such that access to the locked closure flap is substantially blocked so that no lifting force can be applied to the closed and locked closure flap 24.

Figure 12:
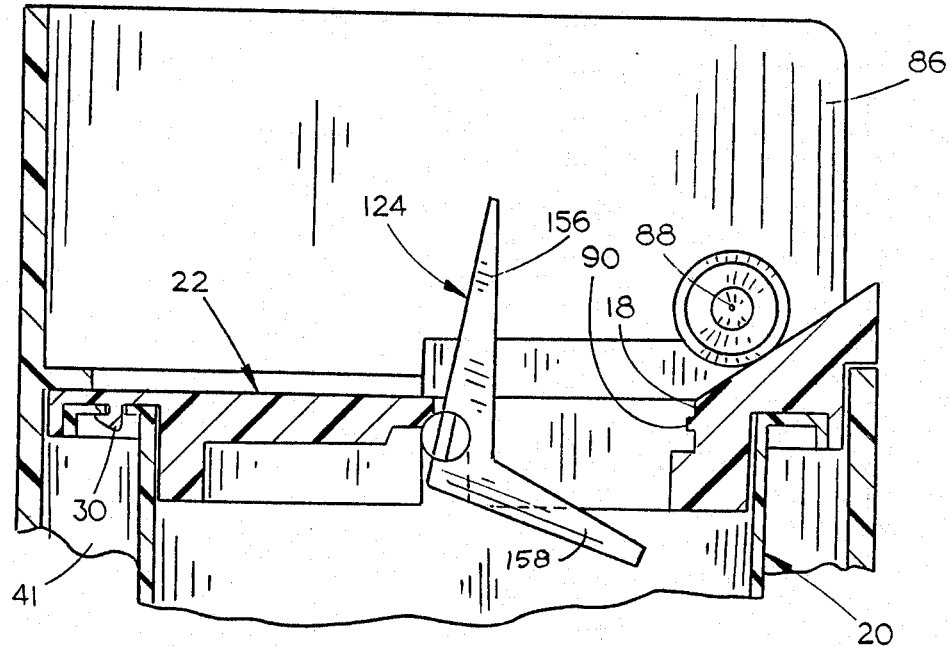
FIG. 12 is a partial side sectional view of the apparatus showing an alternate closure flap to horizontally orient sharps inserted through the top opening.

An alternate closure flap 124 is shown in FIG. 12 which is similar to closure flap 24 but for the angle of inclination of rear wing 158. That angle is such that the rear wing extends downwardly and rearwardly from the closure shaft pivot axis 160 in the closed position of the closure flap but it is pivoted upwardly toward the opening upon pivotal movement of the closure flap to the open position. Thus rear wing 158 extends at least partially across opening 18 in the open position of the closure flap so as to engage sharps inserted through opening 18 for horizontally orienting them as they drop into the receptacle 20. The rear wing performs the second function of closing opening 18 thereby preventing the insertion of a hand into the receptacle when the closure flap is opened.

An important advantage of the sharps container of the invention is that the only surface of the closure flap which is exposed to contamination upon insertion of sharps into the opening is the interior surface which is completely unexposed upon movement of the closure flap to the closed position by the self-closing spring or gravity.

Thus there has been shown and described an improved sharps container which is believed to accomplish all of the stated objects.

We claim:
1. A sharps container comprising,
   a disposable container including a top surface having an elongated opening,
   a closure flap having opposite ends, the length of said closure flap substantially corresponding to the length of said opening,
   means for pivotally supporting said closure flap adjacent said opening for pivotal movement of said flap between an open position permitting the insertion of sharps into said container through said opening and a closed position substantially closing said opening,
   a permanent cabinet including a pair of generally upright spaced-apart end walls having interior and exterior sides and front and rear edges, a front wall extended between the front edges of said end walls, and means for supporting said container within said cabinet between said end walls at a position such that said end walls extend upwardly above the top surface of said container, and
   handle means on the exterior side of at least one end wall, said handle means including means for operatively connecting said handle means to said closure flap for pivotal movement of said flap between said closed and opened positions in response to pivotal movement of said handle means in opposite directions, the hand operating said handle means being protected by the adjacent end wall from sharps being inserted into said opening.
2. The sharps container of claim 1 wherein said disposable container includes a receptacle having an open top, a lid adapted for covering at least a portion of the open top of said receptacle, means for securing said lid on said receptacle and said elongated opening being formed in said lid for the insertion of sharps into said receptacle.

3. The sharps container of claim 1 wherein said means for operatively connecting said handle means to said closure flap includes a closure shaft means connected to said flap at the opposite ends thereof and coacting means on said closure shaft means and handle means for rotation of said closure shaft means and said handle in unison.

4. The sharps container of claim 3 wherein said coacting means on said closure shaft means and handle means comprises a flattened end on said closure shaft and a diametrically extended slot through the pivot axis of said handle means for receiving said flattened end.

5. The sharps container of claim 4 further comprising a handle opening through at least said one end wall in alignment with said closure shaft for pivotally receiving said handle means.

6. The sharps container of claim 5 wherein at least said one end wall includes an elongated guide slot on the interior side thereof, said slot extending from said handle opening to the front edge of said end wall, said guide slot being operative to receive said flattened end of the closure shaft means and to constrain said flattened end to a horizontal orientation for rearward sliding movement in said guide slot toward said handle means.

7. The sharps container of claim 6 further comprising coacting means on said container and handle means for biasing said handle means to a position wherein said diametrically extended slot is horizontally disposed and aligned with said guide slot for receiving said flattened end of the closure shaft means.

8. The sharps container of claim 7 wherein said coacting means comprises a spring means.

9. The sharps container of claim 1 further comprising means for biasing said closure flap to the closed position thereof.

10. The sharps container of claim 1 further comprising spring means operatively connected to said cabinet and handle means for biasing said closure flap to the closed position thereof.

11. The sharps container of claim 1 wherein said closure flap is of such a shape and size that it is biased by gravity toward the closed position thereof.

12. The sharps container of claim 1 wherein said lid includes edges bordering said opening, which edges are inclined downwardly and toward said opening.

13. The sharps container of claim 1 further comprising means for locking said closure flap in the closed position thereof.

14. The sharps container of claim 2 wherein said lid further comprises a forward lip adapted to overlie the top edge of the front wall of said cabinet.

15. The sharps container of claim 2 wherein said receptacle is of a shape adapted for nesting a plurality of receptacles together for storage and shipment.

16. The sharps container of claim 1 wherein the pivot axis for said closure flap is situated adjacent the rearward edge of said elongated opening and said closure flap includes front and rear wings on opposite sides of said pivot axis, said front wing extending across said elongated opening and said rear wing extending generally rearwardly below said top surface of the container in the closed position and said front wing being pivoted upwardly out of said opening and said rear wing being pivoted downwardly into said container upon pivotal movement of the closure flap to the open position.

17. The sharps container of claim 1 wherein the pivot axis for said closure flap is situated adjacent the rearward edge of said elongated opening and said closure flap includes front and rear wings extending generally radially from said pivot axis, said front wing extending across said elongated opening and said rear wing extending generally downwardly below said top surface of the container in the closed position and said front wing being pivoted upwardly out of said opening and said rear wing being pivoted upwardly toward said opening upon pivoted movement of the closure flap to the open position.

18. A sharps container, comprising,
   a receptacle having an open top, a bottom wall, front and rear walls and opposite end walls having interior and exterior sides,
   a lid adapted for covering at least a portion of the open top of said receptacle,
   means for securing said lid on said container,
   said lid having an elongated opening for the insertion of sharps into said container,
   a closure flap having opposite ends, the length of said closure flap substantially corresponding to the length of said opening,
   means for pivotally supporting said closure flap adjacent said opening for pivotal movement of said flap between an open position permitting the insertion of sharps into said container through said opening and a closed position substantially closing said opening, and
   handle means on the exterior side of at least one end wall, said handle means including means for operatively connecting said handle means to said closure flap for pivotal movement of said flap between said closed and open positions in response to pivotal movement of said handle means in opposite directions.

19. The sharps container of claim 18 wherein said lid has a generally flat top surface and at least a substantial portion of said handle means is situated lower than the top surface of said lid.

20. The sharps container of claim 18 wherein said handle includes a connector adjacent one end for connection to said closure flap and an elongated grip extended downwardly and rearwardly from said connector to the closed position of said closure flap and downwardly and forwardly from said connector in the open position of said closure flap.

21. The sharps container of claim 19 further comprising an elongated upward protrusion on the top surface of the lid between said opening and handle means.

22. The sharps container of claim 18 wherein said protrusion is situated at the edge of said opening and presents a top surface inclined downwardly and towards said opening.

23. The sharps container of claim 18 wherein said closure flap is of such a shape and size that it is biased by gravity toward the closed position thereof.

24. The sharps container of claim 23 wherein the pivot axis for said closure flap is situated adjacent the rearward edge of said elongated opening and said closure flap includes front and rear wings on opposite sides of said pivot axis, said front wing extending across said elongated opening and said rear wing extending generally rearwardly below said lid in the closed position, said front wing being pivoted upwardly out of said opening and said rear wing being pivoted downwardly into said receptacle upon pivotal movement of the closure flap to the open position.

25. The sharps container of claim 18 wherein the pivot axis for said closure flap is situated adjacent the rearward edge of said elongated opening and said closure flap includes front and rear wings extending generally radially from said pivot axis, said front wing extending across said elongated opening and said rear wing extending generally downwardly below said top surface of the container in the closed position and said front wing being pivoted upwardly out of said opening and said rear wing being pivoted upwardly toward said opening upon pivoted movement of the closure flap to the open position.

* * * * *